US010133052B2

United States Patent
Jo et al.

(10) Patent No.: US 10,133,052 B2
(45) Date of Patent: Nov. 20, 2018

(54) IMAGE ACQUIRING METHOD AND IMAGE ACQUIRING APPARATUS USING THE SAME

(71) Applicant: Park Systems Corp., Suwon-si, Gyeonggi-do (KR)

(72) Inventors: Ah Jin Jo, Seoul (KR); Ju Suk Lee, Suwon-si (KR); Sang Han Chung, Seoul (KR); Han Aul Noh, Suwon-si (KR)

(73) Assignee: PARK SYSTEMS CORP., Suwon-si, Gyeonggi-do (KR)

( * ) Notice: Subject to any disclaimer, the term of this patent is extended or adjusted under 35 U.S.C. 154(b) by 271 days.

(21) Appl. No.: 14/650,237

(22) PCT Filed: Jun. 26, 2014

(86) PCT No.: PCT/KR2014/005714
§ 371 (c)(1),
(2) Date: Jun. 5, 2015

(87) PCT Pub. No.: WO2014/209043
PCT Pub. Date: Dec. 31, 2014

(65) Prior Publication Data
US 2015/0301329 A1    Oct. 22, 2015

(30) Foreign Application Priority Data

Jun. 27, 2013 (KR) .................. 10-2013-0074792

(51) Int. Cl.
| | |
|---|---|
| G02B 21/36 | (2006.01) |
| G01N 21/95 | (2006.01) |
| G06T 5/50 | (2006.01) |
| G06T 7/00 | (2017.01) |

(52) U.S. Cl.
CPC ....... G02B 21/367 (2013.01); G01N 21/9501 (2013.01); G06T 5/50 (2013.01);
(Continued)

(58) Field of Classification Search
CPC ........ G02B 21/367; G06T 2207/10056; G06T 2207/20224; G06T 2207/30148;
(Continued)

(56) References Cited

U.S. PATENT DOCUMENTS

| | | | |
|---|---|---|---|
| 6,236,057 B1 * | 5/2001 | Shishido | G01N 21/95607 250/208.1 |
| 2006/0079324 A1 | 4/2006 | Watanabe et al. | |
| 2009/0175530 A1 * | 7/2009 | Sjostrom | G01N 21/956 382/152 |

FOREIGN PATENT DOCUMENTS

| | | |
|---|---|---|
| JP | 63-201556 A | 8/1988 |
| JP | 01253639 A | 10/1989 |

(Continued)

OTHER PUBLICATIONS

Office Action dated Aug. 31, 2016 from Japan Patent Office in connection with the counterpart Japan patent application No. 2016-511690.

(Continued)

*Primary Examiner* — Dave Czekaj
*Assistant Examiner* — Berteau Joisil
(74) *Attorney, Agent, or Firm* — Hauptman Ham, LLP

(57) ABSTRACT

An image acquiring method for acquiring an image using a measurement apparatus including an image acquiring means which acquires an image of a surface of a target to be measured in the unit of predetermined size pixels and a moving means capable of moving the target to be measured, the image acquiring method includes: acquiring an image of a first region from the surface of the target to be measured through the image acquiring means; acquiring an image of a second region, which is different from the first region, by moving the target to be measured, through the moving means; acquiring a differential image by subtracting, from
(Continued)

either the image of the first region or the image of the second region, the other image; and overlapping the differential image multiple times.

8 Claims, 17 Drawing Sheets

(52) U.S. Cl.
CPC .. *G06T 7/0004* (2013.01); *G06T 2207/10056* (2013.01); *G06T 2207/10061* (2013.01); *G06T 2207/20216* (2013.01); *G06T 2207/20221* (2013.01); *G06T 2207/20224* (2013.01); *G06T 2207/30148* (2013.01)

(58) Field of Classification Search
CPC ......... G06T 7/0004; G06T 2207/20221; G06T 5/51; G06T 2207/10061; G06T 2207/20216; G01N 21/9501
See application file for complete search history.

(56) References Cited

FOREIGN PATENT DOCUMENTS

| | | |
|---|---|---|
| JP | 6063984 B2 | 8/1994 |
| JP | 08-146137 A | 6/1996 |
| JP | 2005077272 A | 3/2005 |
| JP | 2007-248325 A | 9/2007 |
| JP | 2009115613 A | 5/2009 |
| JP | 2010151697 A | 7/2010 |

OTHER PUBLICATIONS

International Search Report for PCT/KR2014/005714 dated Sep. 26, 2014.
Extended European Search Report dated Aug. 1, 2016 in connection with the counterpart European Patent Application No. 14818687.7-1562.

* cited by examiner (a)

(b)

(c)

IMAGE ACQUIRING METHOD AND IMAGE ACQUIRING APPARATUS USING THE SAME

CROSS REFERENCE TO RELATED APPLICATION

This application claims the priority of Korean Patent Application No. 2013-0074792, filed on Jun. 27, 2013 in the KIPO (Korean Intellectual Property Office). Further, this application is the National Phase application of International Application No. PCT/KR2014/005714 filed Jun. 26, 2014, which designates the United States and was published in Korean.

TECHNICAL FIELD

The present invention relates to an image acquiring method and an image acquiring apparatus using the same, and more particularly, to an image acquiring method, of which more specifically image defects of a flat surface of a target, such as a wafer, is measured, and an image acquiring apparatus using the same.

BACKGROUND ART

A Scanning Probe Microscope (SPM) refers to a microscope that measures surface characteristics of a sample so as to be shown as a 3D image while allowing a nanoprobe manufactured by a MEMS process to scan over a surface of the sample (scanning). The SPM is subdivided into an Atomic Force Microscope (AFM), a Scanning Tunneling Microscope (STM), and the like depending on a measurement method.

Generally, the SPM such as the AFM uses an optical vision system in order to determine a measurement position of a probe. The optical vision system includes a digial camera using an image sensor, such as a charged-coupled device (CCD) or a complementary metal-oxide semiconductor (CMOS), an object lens arranged toward a surface side of a target to be measured, and a body tube. Such body tube is configured to optically connect the camera with the object lens and transfer an image falling on the object lens to the image sensor of the camera.

When a surface of the target is measured using the SPM, the above-described optical vision system is moved in a Z-direction (up and down direction) using a precision stage so as to be focused on the surface of the target. Therefore, an image of the surface of the target falls on the image sensor, and a signal output from the camera is displayed on a display device such as a monitor. Thus, a user can observe the surface of the target, which is enlarged according to a magnification of the object lens.

Then, while the surface of the target is observed using the optical vision system, the target is moved to a desired position using an XY-stage configured to move the target in X and Y directions. Then, the target is measured by the SPM.

Such a SPM, particularly an AFM, has often been used for a defect review of a flat target to be measured such as a wafer. Such a defect review is conducted by checking a position of a defect using an optical vision system, moving a probe (actually moving the target) to the position, and imaging a detailed shape of the defect through the probe.

However, if the defect of a flat surface of the target to be measured such as a wafer has a small width, it is difficult to observe the presence of the defect with the optical vision system. Therefore, a defect review cannot be conducted or may be restrictively conducted by the SPM in many cases.

FIG. 1a is a surface image of a wafer observed with an optical vision system. FIG. 1b is a background image acquired by image-processing the surface image of FIG. 1a using a low pass filter. FIG. 1c is an image acquired by subtracting the background image from the image of FIG. 1a. FIG. 1d is an image acquired by overlapping the image of FIG. 1c 32 times, and FIG. 1e is an image acquired by overlapping the image of FIG. 1c 512 times.

Referring to FIG. 1a, it is difficult to find a defect on the wafer with the naked eye. Therefore, typically, a high-frequency noise component is removed using a low pass filter so as to acquire the background image as shown in FIG. 1b. Then, the background image is removed from the image of FIG. 1a so as to acquire the image as shown in FIG. 1c. However, referring to FIG. 1c, it can be seen that even in this case, it is difficult to observe defects indicated by arrows with the naked eye.

Accordingly, in order to achieve an averaging effect, the image of FIG. 1c is overlapped multiple times (32 times) so as to acquire the image of FIG. 1d. Since a signal-to-noise ratio (SNR) is proportional to the square root of the number of times of overlapping, if the image is repeatedly overlapped, the defects are clearly visible compared to the noise. Therefore, a defect indicated by an arrow in FIG. 1d is more clearly visible, but any defect smaller than this defect is still invisible.

Further, referring to FIG. 1e, such overlapping has a marginal effect. Thus, even when the image is overlapped 512 times, a defect is not more clearly visible than the defect in the image overlapped 32 times.

Therefore, even if an image is overlapped, there is a limit in observing a defect with an optical vision system. Thus, a defect, to which a defect review needs to be conducted may often be overlooked. It is considered that such a problem is caused by non-uniformity between pixels of an image sensor, by which non-uniformity is caused depending on a position of an optical system.

DISCLOSURE

Technical Problem

The present invention is conceived to solve the above-described problem. An object of the present invention is to provide an image acquiring method, specifically of which image defects, such as a wafer, of a flat surface of a target can be measured, and an image acquiring apparatus using the same.

However, the objects of the present invention are not limited to the aforementioned objects, and other objects, which are not mentioned above, will be apparent to a person having ordinary skill in the art from the following description.

Technical Solution

According to an aspect of the present invention to achieve the above-described object, there is provided an image acquiring method for acquiring an image using a measurement apparatus. Such apparatus includes an image acquiring means which acquires an image of a surface of a target to be measured in the unit of predetermined size pixels and a moving means capable of moving the target to be measured. The image acquiring method includes: acquiring an image of a first region from the surface of the target to be measured through the image acquiring means; acquiring an image of a second region, which is different from the first region, by moving the target to be measured, through the moving means; acquiring a differential image by subtracting, from either the image of the first region or the image of the second region, the other image; and overlapping the differential image multiple times.

According to another aspect of the present invention to achieve the above described object, there is provided an image acquiring method for acquiring an image using a measurement apparatus. Such apparatus includes an image acquiring means which acquires an image of a surface of a target to be measured in the unit of predetermined size pixels and a moving means capable of moving the target to be measured. The image acquiring method includes: acquiring an image of a first region from the surface of the target to be measured N times (herein, N is an integer of 2 or more) through the image acquiring means; acquiring a first summed image by summing N images of the first region; moving the target to be measured to a second region, which is different from the first region, through the moving means; acquiring an image of the second region from the surface of the target to be measured M times (herein, M is an integer of 2 or more) through the image acquiring means; acquiring a second summed image by summing M images of the second region; and acquiring a differential image by subtracting, from either the first summed image or the second summed image, the other summed image.

Further, according to another feature of the present invention, a distance between the first region and the second region is greater than a resolution of the image acquiring means.

Furthermore, according to yet another feature of the present invention, a distance between the first region and the second region is smaller than a size of a target to be detected.

Also, according to still another feature of the present invention, the N is identical to the M.

According to yet another aspect of the present invention to achieve the above-described object, there is provided an image acquiring apparatus including: an image acquiring means which acquires an image of a surface of a target to be measured in the unit of predetermined size pixels; a moving means capable of moving the target to be measured; and a control unit that receives the image from the image acquiring means and performs an image process, and controls an operation of the moving means, and the control unit processes the image of the surface of the target to be measured by acquiring an image of a first region from the surface of the target to be measured through the image acquiring means, acquiring an image of a second region, which is different from the first region, by moving the target to be measured, through the moving means, acquiring a differential image by subtracting, from either the image of the first region or the image of the second region, the other image, and overlapping the differential image multiple times.

According to still another aspect of the present invention to achieve the above-described object, there is provided an image acquiring apparatus including: an image acquiring means which acquires an image of a surface of a target to be measured in the unit of predetermined size pixels; a moving means capable of moving the target to be measured; and a control unit that receives the image from the image acquiring means and performs an image process, and controls an operation of the moving means, and the control unit processes the image of the surface of the target to be measured by acquiring an image of a first region from the surface of the target to be measured N times (herein, N is an integer of 2 or more) through the image acquiring means, calculating a first summed image by summing N images of the first region, moving the target to be measured to a second region, which is different from the first region, through the moving means, acquiring an image of the second region from the surface of the target to be measured M times (herein, M is an integer of 2 or more) through the image acquiring means, calculating a second summed image by summing M images of the second region, and calculating a differential image by subtracting, from either the first summed image or the second summed image, the other summed image.

Further, according to another feature of the present invention, the image acquiring means is an imaging apparatus using a CCD or a CMOS.

According to still another aspect of the present invention to achieve the above-described object, there is provided an atomic force microscope (AFM) including the above-described image acquiring apparatus.

Advantageous Effects

According to the present invention, in the image acquiring method and the image acquiring apparatus using the same, it is possible to measure more specifically image defects, such as a wafer, of a flat surface of a target. Thus, it is possible to effectively conduct a defect review.

DESCRIPTION OF DRAWINGS

FIG. 1c is an image acquired by subtracting the background image from the image of FIG. 1a;

BEST MODE

Figure 1A:
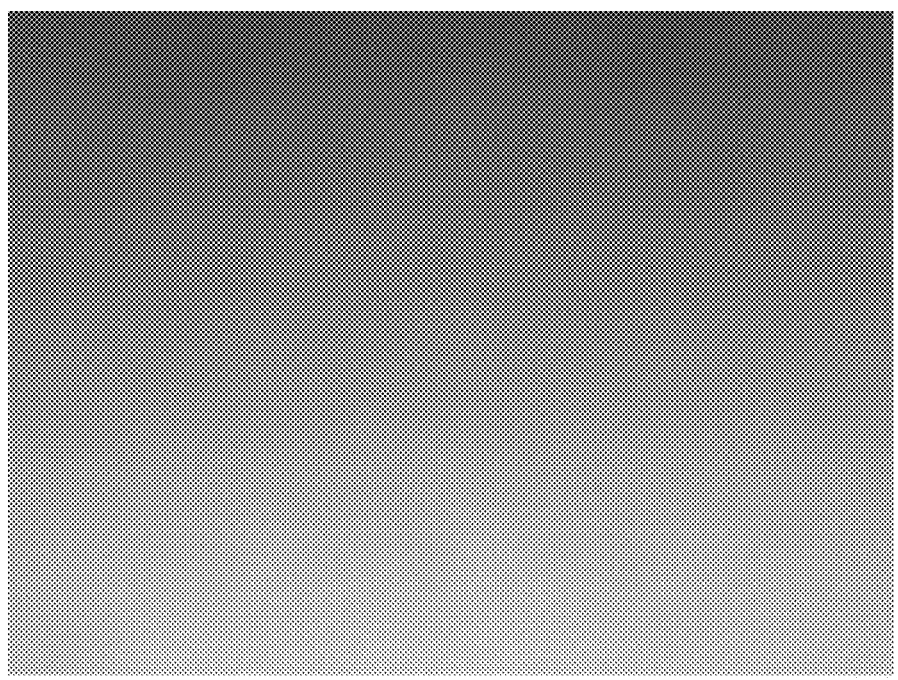
FIG. 1a is a surface image of a wafer observed with an optical vision system.
Figure 1B:
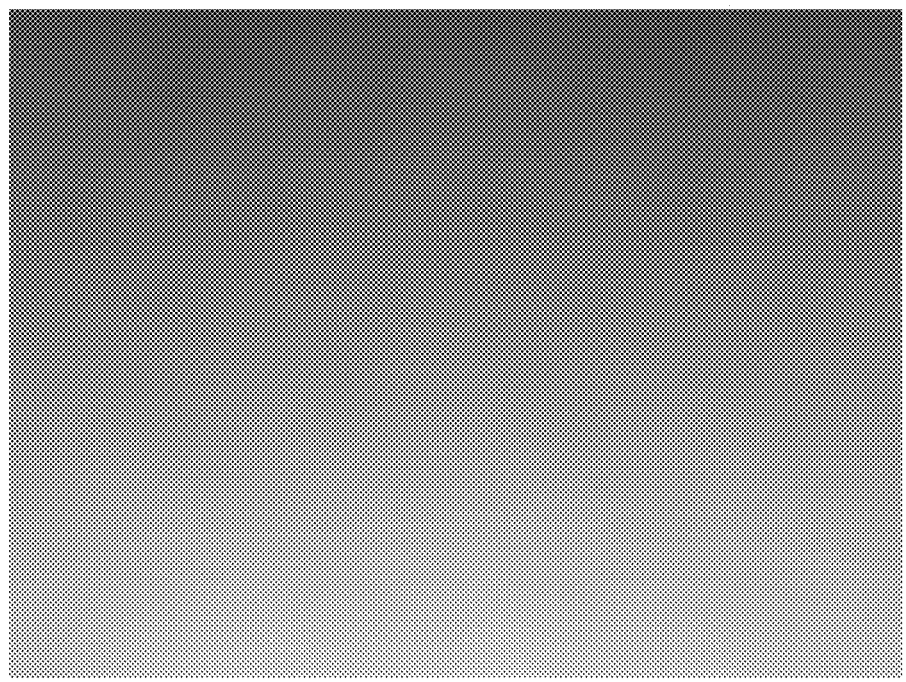
FIG. 1b is a background image acquired by image-processing the surface image of FIG. 1a using a low-pass filter.
Figure 1C:
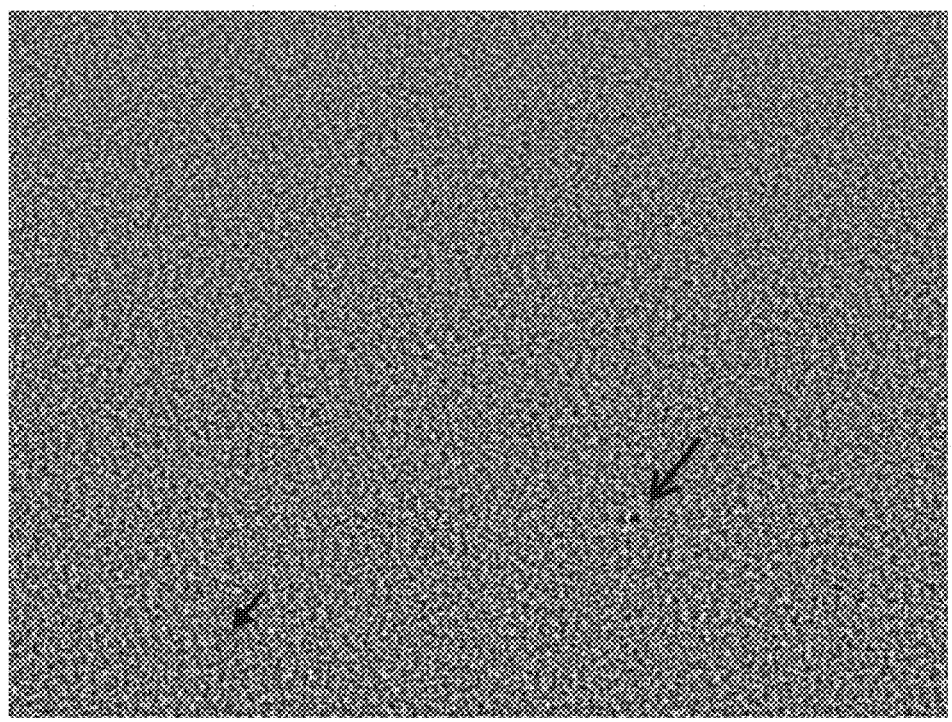
Figure 1D:
FIG. 1d is an image acquired by overlapping the image of FIG. 1c 32 times.
Figure 1E:
FIG. 1e is an image acquired by overlapping the image of FIG. 1c 512 times.

Advantages and features of the present invention, and methods for accomplishing the same will be more clearly understood from exemplary embodiments described below with reference to the accompanying drawings. However, the present invention is not limited to the following exemplary embodiments but may be implemented in various different forms. The exemplary embodiments are defined only to complete disclosure of the present invention and to fully provide a person having ordinary skill in the art to which the present invention pertains with the category of the invention.

When an element or layer is referred to as being "on" another element or layer, it may be directly on the other element or layer, or intervening elements or layers may be present.

Although the terms "first", "second", and the like are used for describing various components, these components are not confined by these terms. These terms are merely used for distinguishing one component from the other components. Therefore, a first component to be mentioned below may be a second component in a technical concept of the present invention.

Throughout the whole document, the same reference numerals represent the same elements, respectively.

Since size and thickness of each component illustrated in the drawings are represented for convenience in explanation, the present invention is not necessarily limited to the drawings.

The features of various embodiments of the present invention can be partially or entirely bonded to or combined with each other and can be interlocked and operated in technically various ways as can be fully understood by a person having ordinary skill in the art, and the embodiments can be carried out independently of or in association with each other.

Hereinafter, an image acquiring method and an image acquiring apparatus using the same according to the present invention will be described with the accompanying drawings.

Figure 2:
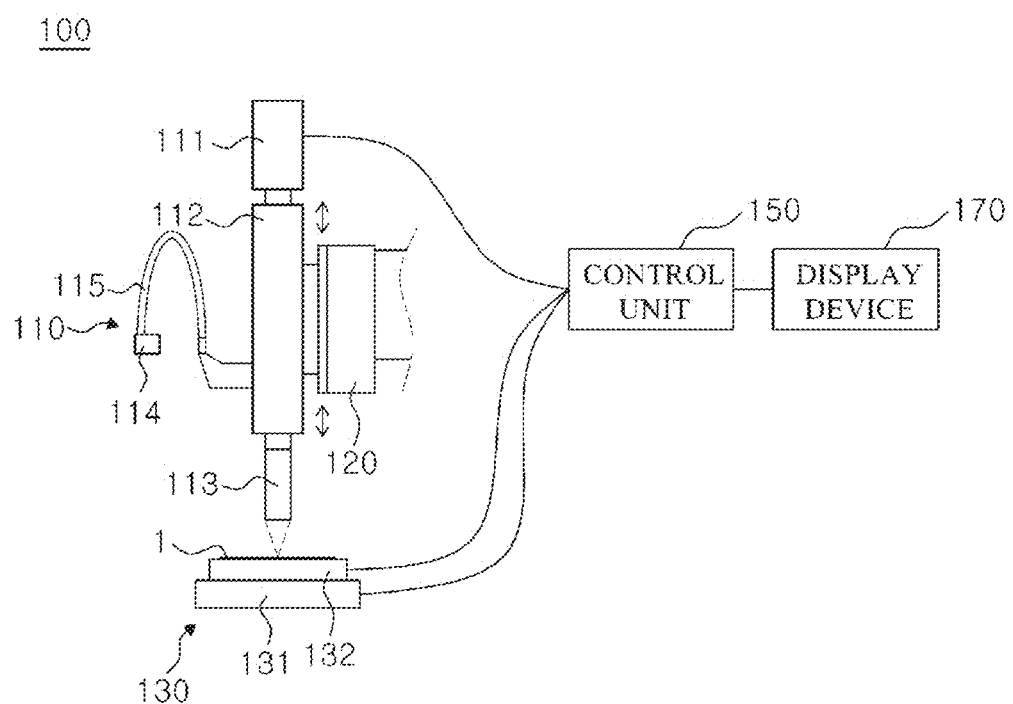
FIG. 2 is a schematic concept diagram of an image acquiring apparatus according to an exemplary embodiment of the present invention.

FIG. 2 is a schematic concept diagram of an image acquiring apparatus according to an exemplary embodiment of the present invention. Referring to FIG. 2, there will be described an image acquiring apparatus 100 to which an image acquiring method of the present invention can be applied.

The image acquiring apparatus 100 according to an exemplary embodiment of the present invention includes: an image acquiring means 110; a moving means 130; a control unit 150; and a display device 170.

The image acquiring means 110 is configured to optically acquiring an image of a surface of a target 1 to be measured in the unit of predetermined size pixels, and includes a digital camera 111, a body tube 112, an object lens 113, and a light source 114 in the present exemplary embodiment.

The digital camera 111 refers to a camera equipped with an image sensor such as a CCD or a CMOS and digitizes an image in the unit of pixel and transmits the digitized image to the control unit 150. The camera 111 may use any digital image sensor, and cameras having various resolutions can be applied. For example, as the digital camera 111, a XCL-5005CR manufactured by SONY Corporation, Japan may be used.

The camera 111 is mounted on the body tube 112 and the object lens 113 is provided under the body tube 112. Thus, the body tube 112 transmits an image magnified by the object lens 113 to the image sensor of the camera 111.

Further, the body tube 112 is connected with an optical fiber 115 and irradiates light from the light source 114 to the inside of the optical fiber 115 and thus enables an image of the surface of the target 1 to be visible.

The object lens 113 is configured to magnify an image of the surface of the target 1 and may have various magnifications. That is, various object lenses having magnifications of 5, 10, and 20 may be applied depending on the purpose of use. For example, when a surface of a wafer is observed, an object lens having a magnification of 10 may be used.

The image acquiring means 110 can be vertically moved by a Z stage 120. The Z stage 120 is a linear moving stage, and may employ various moving stages. For example, a ball screw-type transfer stage may be used. A position of the image acquiring means 110 is vertically adjusted by using the Z stage 120 such that an image falls on the object lens 113.

The moving means 130 refers to a means configured to move the target 1 in an X-Y plane, and may include a long-distance transfer device 131 and a short-distance transfer device 132.

The long-distance transfer device 131 has a relatively low accuracy in transfer but can perform a long-distance transfer in a short time, and may be, for example, a well-known ball screw-type transfer stage.

Meanwhile, the short-distance transfer device 132 has a high accuracy in transfer and can perform a short-distance transfer, and may be, for example, an X-Y scanner which is used in an atomic force microscope. Herein, the X-Y scanner refers to a piezo driving scanner configured to XY scan a target to be measured, and may be, for example, an X-Y scanner manufactured by Park Systems Corporation. Details thereof are disclosed at the website of Park Systems Corporation (www.parkafm.com).

Any one of the long-distance transfer device 131 and the short-distance transfer device 132 may be used, but it is desirable to use both devices for rapid and accurate transfer.

The control unit 150 controls the image acquiring means 110 and the moving means 130 and processes image data acquired from the image acquiring means 110. Then, the control unit 150 displays an image of the surface of the target 1 on the display device 170. A controlling method using the control unit 150 will be described later in detail.

The display device 170 refers to a device configured to display the image processed by the control unit 150 so as to be visible to an external user, and may use a well-known LCD monitor, CRT monitor, OLED monitor, or the like.

Hereinafter, an image acquiring method using the image acquiring apparatus 100 configured as described above will be described in detail.

Figure 3:
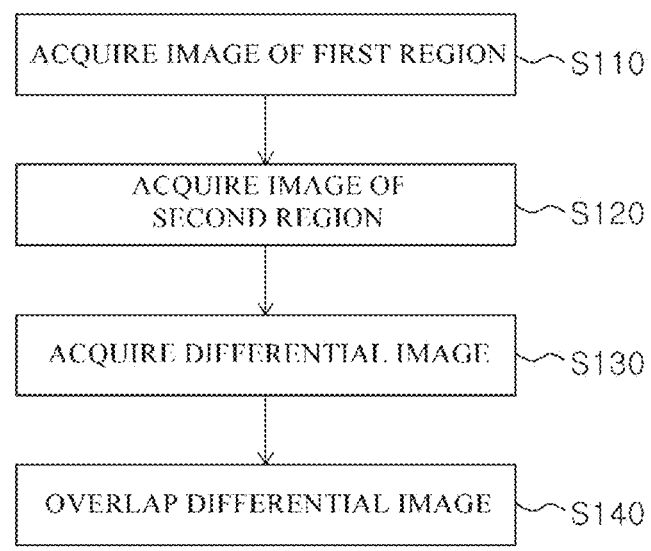
FIG. 3 is a flowchart of an image acquiring method according to an exemplary embodiment of the present invention.
Figure 4A:
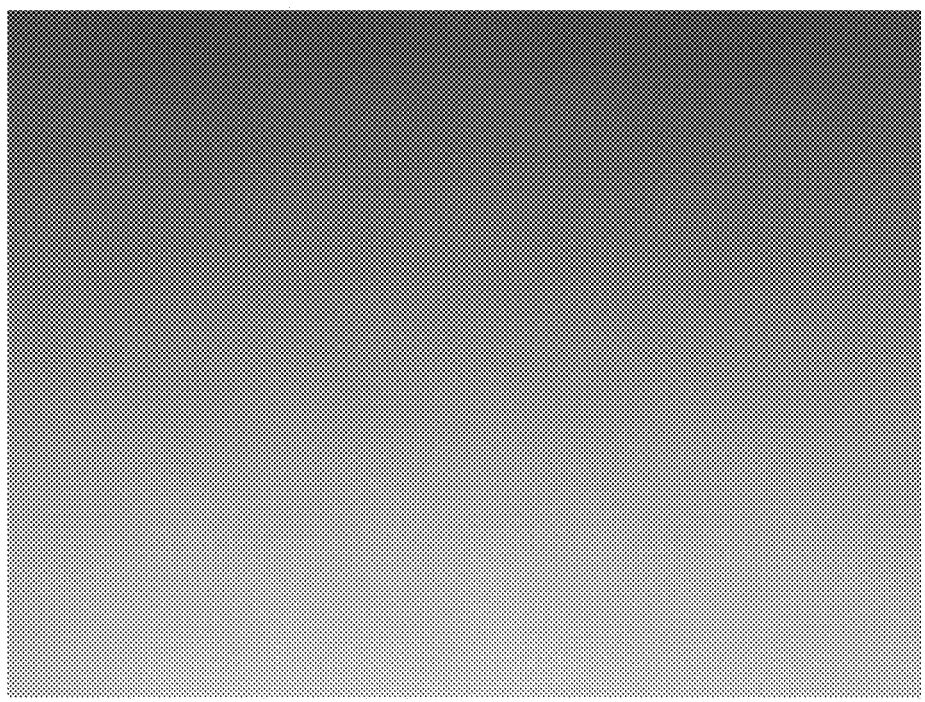
FIG. 4a is an image of a first region from a wafer.
Figure 4B:
FIG. 4b is an image of a second region from the wafer.
Figure 5:
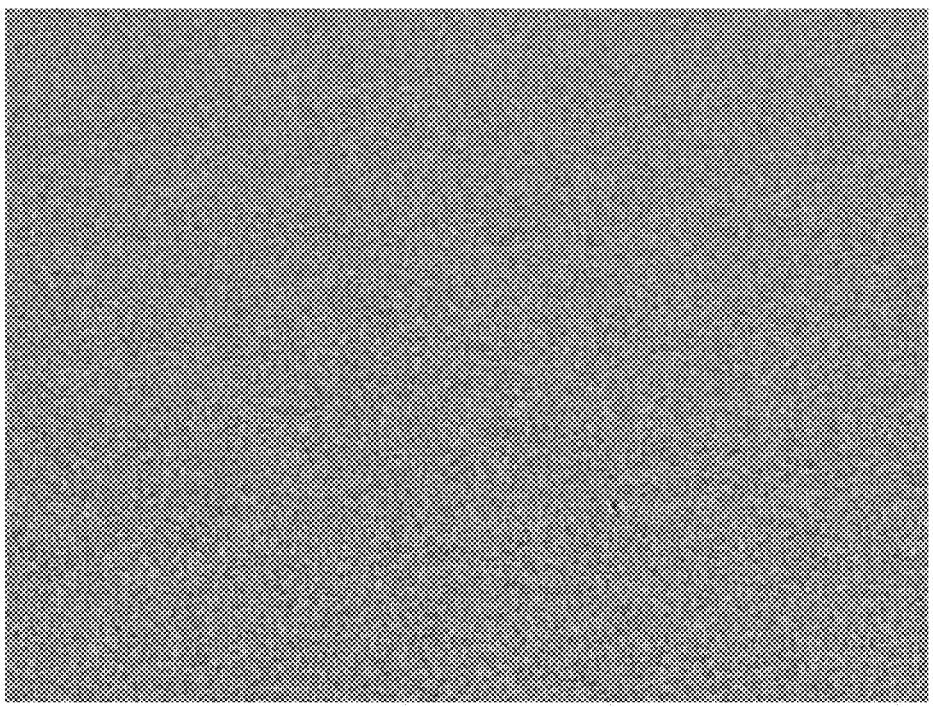
FIG. 5 is a differential image between the image of FIG. 4a and the image of FIG. 4b.
Figure 6A:
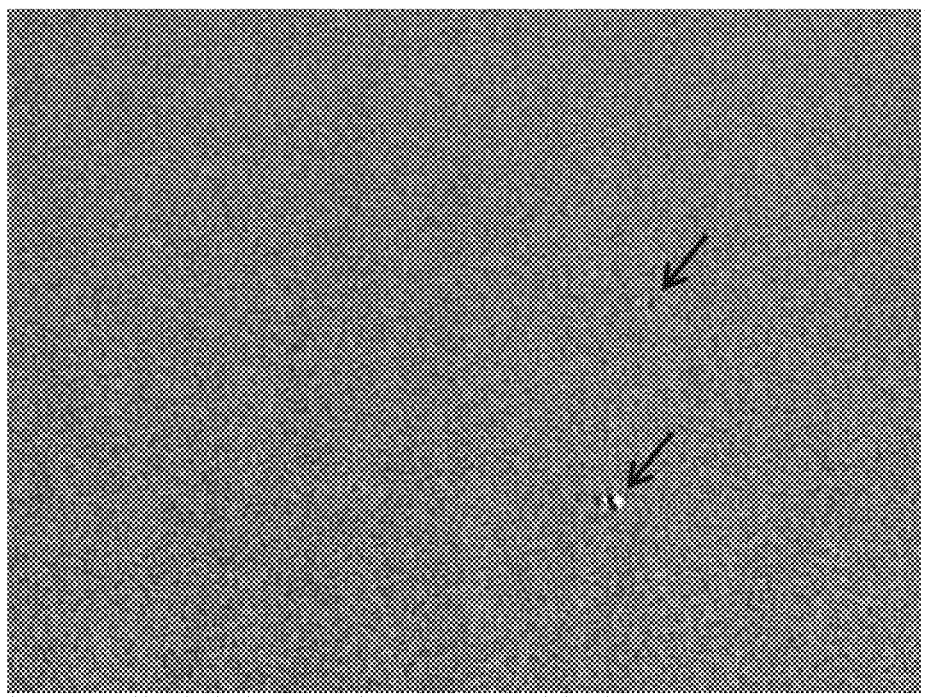
FIG. 6a is an image acquired by overlapping the differential image of FIG. 5 32 times.
Figure 6B:
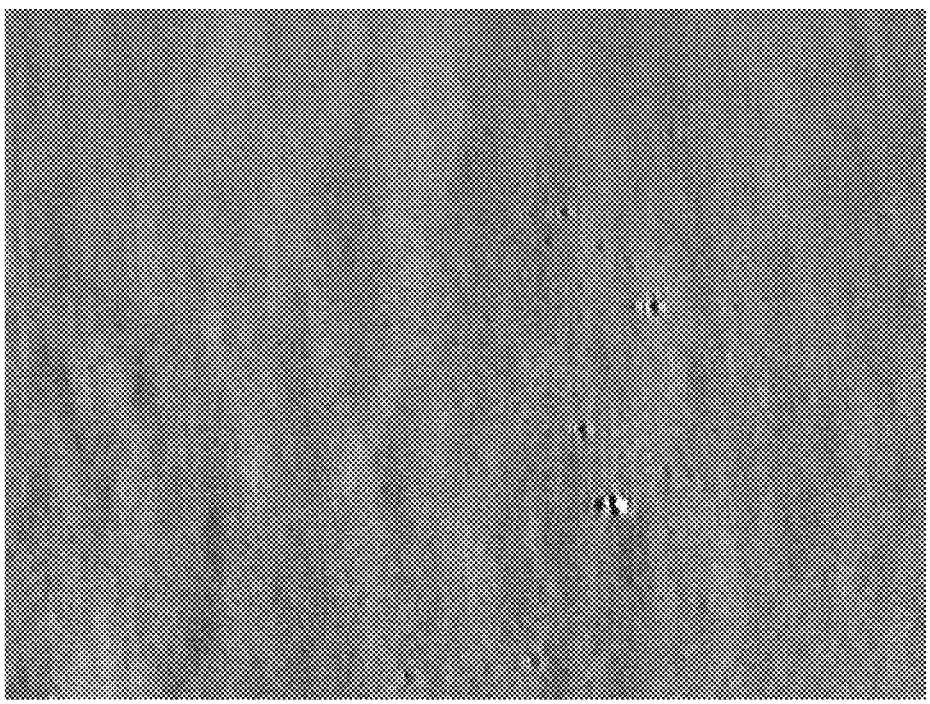
FIG. 6b is an image acquired by overlapping the differential image of FIG. 5 512 times.

FIG. 3 is a flowchart of an image acquiring method according to an exemplary embodiment of the present invention. Further, FIG. 4a is an image of a first region from a wafer, and FIG. 4b is an image of a second region from the wafer. Furthermore, FIG. 5 is a differential image between the image of FIG. 4a and the image of FIG. 4b. Also, FIG. 6a is an image acquired by overlapping the differential image of FIG. 5 32 times, and FIG. 6b is an image acquired by overlapping the differential image of FIG. 5 512 times.

For reference, the images of FIG. 4a and FIG. 4b to be described below are acquired by using a XCL-5005CR manufactured by SONY Corporation as the camera 111 and magnified by the object lens 113 having a magnification of 10. The camera 111 has a cell size of 3.45 μm in width and length, an image size of 2448×2050 (5,018,400 pixels), and a frame rate of 15 fps.

Referring to FIG. 3, the image acquiring method according to the present exemplary embodiment includes: a step of acquiring an image of a first region (S110); a step of acquiring an image of a second region (S120); a step of acquiring a differential image (S130); and a step of overlapping the differential image (S140).

The step of acquiring an image of a first region (S110) is a step for acquiring an image of an arbitrary first region from the surface of the target 1. The image of the first region may be acquired as illustrated in FIG. 4a. The image illustrated in FIG. 4a is acquired by capturing one frame image acquired by the camera 111 of the image acquiring means 110 and is displayed on the display device 170.

Then, the image of the second region illustrated in FIG. 4b is acquired (S120). The second region is different from the first region, and a region most of which is overlapped with the first region but a part of which is not overlapped with the first region can be the second region. Further, the moving means 130 is configured to transfer the target from the first region to the second region, and particularly, the short-distance transfer device 132 can be more properly used.

In the present exemplary embodiment, the second region is set to a region corresponding to an image acquired by the image acquiring means 110 after moving the target 1 1 μm to the right side in FIG. 4a with the moving means 130. Herein, various methods for setting the second region will be described later.

Referring to FIG. 4a and FIG. 4b, it is difficult to find a defect on the wafer for the target 1 with the naked eye. Therefore, an image process to be described later is performed by the control unit 150.

After the step S120, a differential image is acquired by subtracting, from either the image of the first region or the image of the second region, the other image (S130).

An image subtraction is performed for each pixel by dividing raw data of a pixel at a position (i,j) of the first region by raw data of a pixel at a position (i,j) of the second region. The image of FIG. 5 is acquired by dividing a gray scale value using data of FIG. 4a and FIG. 4b previously converted into gray scale. Such subtraction can be performed by various methods. For example, there is a method of dividing each of R value, G value, and B value and converting an average into gray scale, and there is a method of dividing only a value of a G channel.

Although the flattened image of FIG. 5 is acquired by subtraction, it is still difficult to find a defect with the naked eye. Thus, after the step S130, the differential image of FIG. 5 is overlapped (S140).

In the present step, the image is overlapped by summing a gray scale value of each cell. As the number of times of overlapping increases, a defect is more clearly visible. As compared with a case where the image is overlapped 32 times as shown in FIG. 6a, when the image is overlapped 512 times as shown in FIG. 6b, more defects are visible. The number of times of overlapping can be determined in various ways in consideration of a size of a defect to be checked.

Referring to FIG. 6b, it is possible to observe defects which cannot be observed from FIG. 4a and FIG. 4b. Therefore, a defect review can be conducted on a small defect by the atomic force microscope, and, thus, it is possible to conduct a defect review in more detail.

Figure 7:
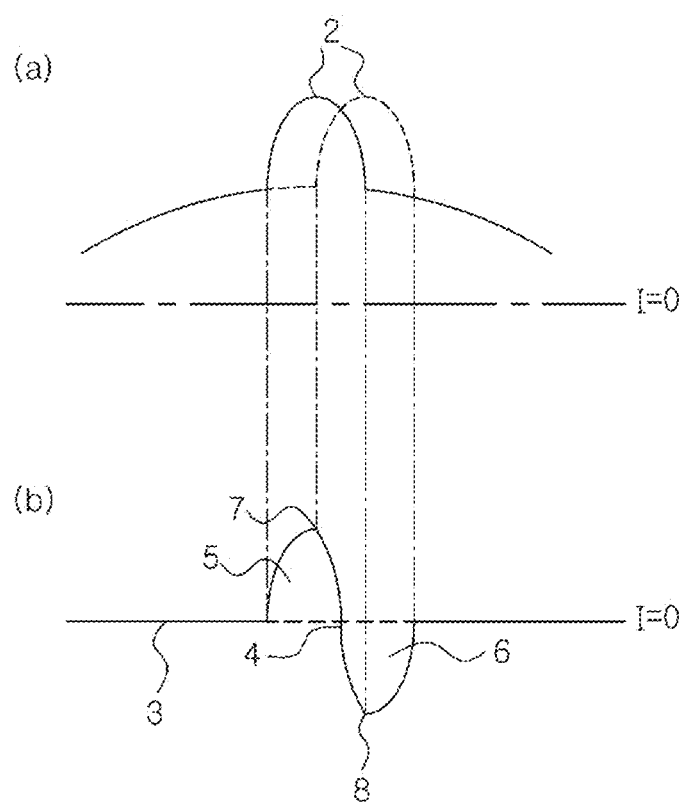
FIG. 7 provides schematic side views of a defect of a target to be measured.

FIG. 7 provides schematic side views of a defect of a target to be measured. In particular, FIG. 7(a) is a diagram illustrating a defect corresponding to FIG. 4a and FIG. 4b, and FIG. 7(b) is a diagram illustrating a differential image thereof.

Referring to FIG. 7, the reason why a defect can be more clearly observed from the image acquired by the image acquiring method according to the present invention will be described.

Referring to FIG. 7(a), in the image of the first region (illustrated by a solid line) and the image of the second region (illustrated by a dotted line), a defect 2 is imaged to be overlapped and not overlapped in certain parts. Herein, even if the target 1 is moved, a background image is measured as being overlapped due to non-uniformity of the sensor and the optical system and the like, and, thus, the image is measured as if only the defect 2 is moved.

Referring to FIG. 7(b), a differential image can be acquired by subtracting the image of the second region from the image of the first region. In the differential image, the background image is completely removed and a signal intensity I of a reference line 3 of a periphery of the defect 2 is converged to 0. Further, in the differential image, a point imaged to be higher than the reference line 3 and a point imaged to be lower than the reference line 3 are positioned to be adjacent to each other. Further, a point 4 where a gray scale value of the image is sharply changed is present between the two points, and, thus, the image is illustrated as being reversed. That is, a region 5 displayed as being brighter than the reference line 3 and a region 6 displayed as being darker than the reference line 3 are positioned to be adjacent to each other.

Referring to FIG. 7(b) again, in the differential image, the background image is deformed to be as flat as the reference line 3 and a point 7 displayed as being the brightest. Also, a point 8 displayed as being the darkest are positioned to be adjacent to each other. Thus, if image overlapping is performed, the background image is not amplified by overlapping and only a difference in a gray scale value of the defect 2 is amplified. Therefore, as compared with a conventional method in which a single image is acquired and overlapped, with a smaller number of times of overlapping, a higher difference in a gray scale value, i.e., a higher difference in brightness, can be acquired while reducing ins and outs of the background. Thus, a visibility is excellent.

Figure 8:
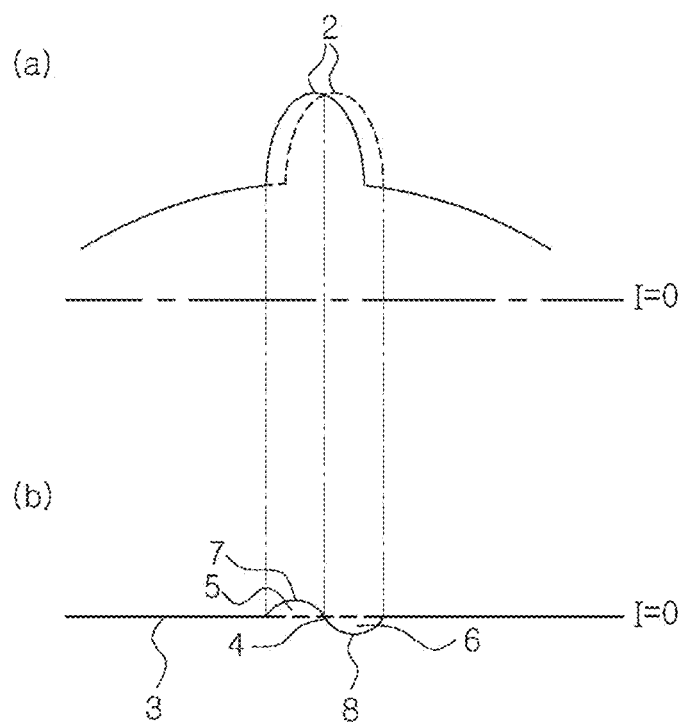
FIG. 8 provides schematic side views of a defect of a target to be measured if a distance between the first region and the second region is smaller than a resolution.
Figure 9:
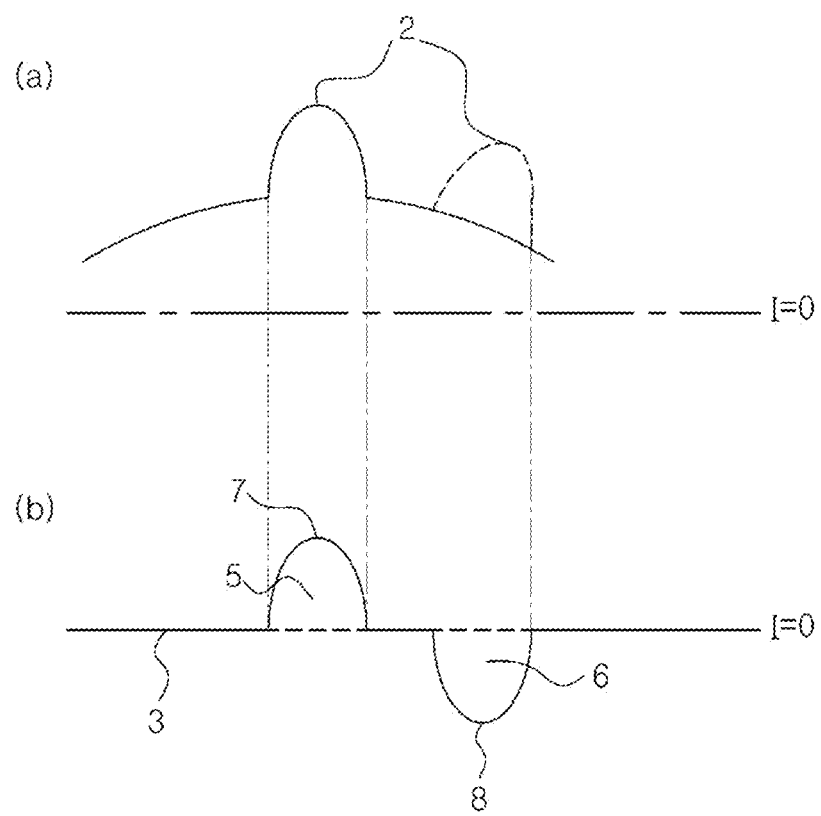
FIG. 9 provides schematic side views of a defect of a target to be measured if a distance between the first region and the second region is greater than a size of the defect.

FIG. 8 provides schematic side views of a defect of a target to be measured if a distance between the first region and the second region is smaller than a resolution. FIG. 9 provides schematic side views of a defect of a target to be measured if a distance between the first region and the second region is greater than a size of the defect.

Referring to FIG. 8 and FIG. 9, there will be described a distance between the first region and the second region for effectively observing the defect 2.

In the present exemplary embodiment, theoretically, a region displayed in a cell of the camera 111 has a size of 3.45 μm in width and length, and the target 1 is displayed as being magnified by the object lens 113 having a magnification of 10. Thus, actually, a region displayed in a cell of the camera 111 has a size of 0.345 μm in width and length. The camera 111 acquires data in the unit of pixel, and, thus, a size of a pixel can be the smallest in visible size, i.e., resolution. Therefore, theoretically, a resolution of the image acquiring apparatus 100 of the present exemplary embodiment is 0.345 μm.

However, this is just an example for obtaining a resolution. The resolution refers to the smallest length unit visible by the image acquiring means 110. That is, the resolution can be theoretically calculated as described above, and can be limited by an optical characteristic of the object lens 113, a quality of the optical system, and the like. For example, if a resolution of the object lens 113 is limited to 1 μm due to various known causes (an Airy disk diameter depending on a numerical aperture NA, and the like), even if a resolution of the camera 111 is smaller than 1 μm, the resolution of the image acquiring apparatus 100 can be limited to 1 μm, which is the resolution of the object lens 113.

As illustrated in FIG. 8, when the first region (solid line) and the second region (dotted line) are separated within a range of the resolution, if a differential image as illustrated in FIG. 8(b) is acquired by subtracting the image of the first region and the image of the second region, a difference in brightness (i.e., a difference in signal intensity) between the point 7 displayed as being the brightest and the point 8 displayed as being the darkest is very small. Thus, it is more difficult to distinguish a defect as compared with a case where a defect is measured as it is. Therefore, preferably, the distance between the image of the first region and the image of the second region is greater than at least the resolution of the image acquiring apparatus 100.

On the other hand, as illustrated in FIG. 9, if the first region (solid line) and the second region (dotted line) are separated so as not to overlap the defect 2, the point 7 displayed as being the brightest and the point 8 displayed as being the darkest in the differential image are not positioned to be adjacent to each other as illustrated in FIG. 9(b). Thus, the point 4 where a gray scale value of the image is sharply changed as illustrated in FIG. 7(b) is not present. Therefore, visibility is decreased.

Accordingly, preferably, the target 1 may be moved longer than at least a resolution of the image acquiring means 110 by the moving means 130. Further, preferably, in consideration of a size (i.e., widths in X and Y directions) of the defect, the target 1 may be moved shorter than the size of the defect 2 by the moving means 130. Herein, the resolution varies depending on a kind of the camera 111 and a magnification of the object lens 113, and, thus, it can be determined according to the specifications of the camera 111 and the object lens 113.

In the present exemplary embodiment, the camera 111 has a resolution of 0.345 μm and the object lens 113 has a resolution of 1 μm. Since the resolution of the image acquiring apparatus 100 is determined as 1 μm, the second region is imaged by moving the target 1 1 μm to the right side in the first region, and, thus, a visibility of a defect having a size of 1 μm or more is increased. The distance between the first region and the second region can be set in various ways depending on a size of a defect to be measured.

Meanwhile, in the present exemplary embodiment, it has been described that the first region and the second region are separated from each other in a transverse direction, but they are not limited thereto. The first region and the second region may be disposed in a vertical direction or may be separated from each other at a predetermined angle.

Figure 10:
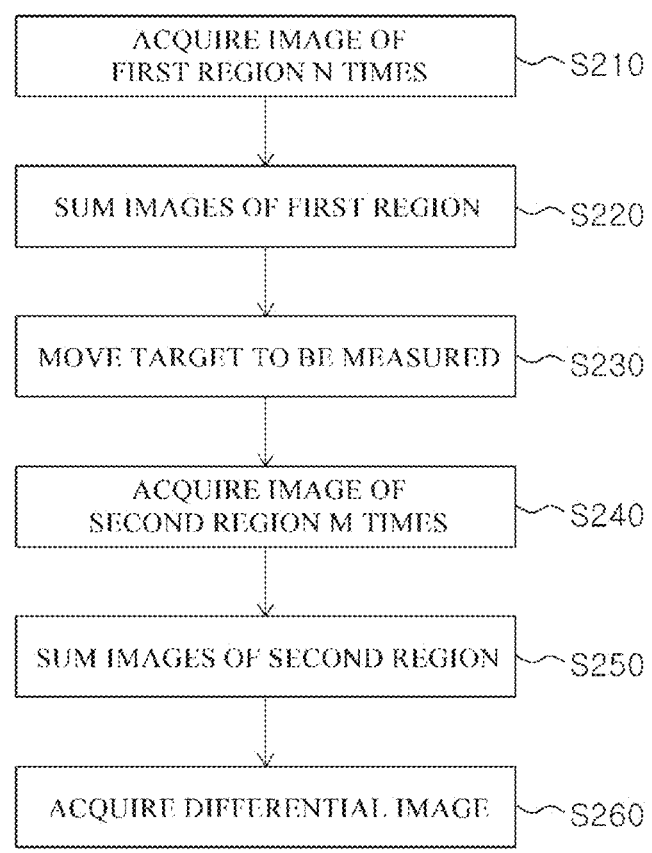
FIG. 10 is a flowchart of an image acquiring method according to another exemplary embodiment of the present invention.
Figure 11:
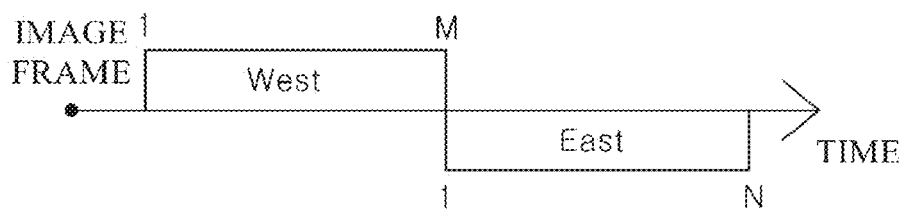
FIG. 11 is a time flowchart illustrating various modification examples of the image acquiring method illustrated in FIG. 10.
Figure 11:
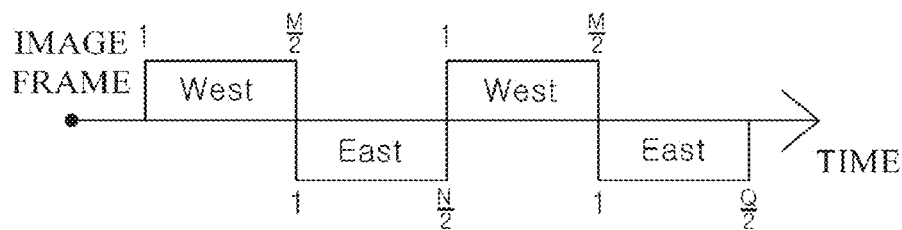
Figure 11:
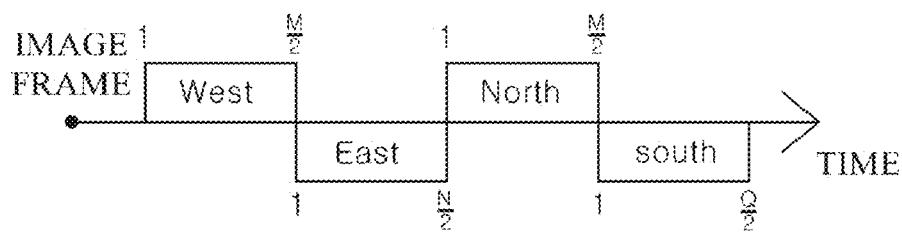

FIG. 10 is a flowchart of an image acquiring method according to another exemplary embodiment of the present invention, and FIG. 11 is a time flowchart illustrating various modification examples of the image acquiring method illustrated in FIG. 10.

Referring to FIG. 10, the image acquiring method according to another exemplary embodiment of the present invention includes: acquiring an image of a first region N times (herein, N is an integer of 2 or more) (S210); acquiring a first summed image by summing images of the first region (S220); moving the target 1 to a second region, which is different from the first region, through the moving means 130 (S230); acquiring an image of the second region M times (herein, M is an integer of 2 or more) (S240); acquiring a second summed image by summing images of the second region (S250); and acquiring a differential image by subtracting, from either the first summed image or the second summed image, the other summed image (S260).

In the image acquiring method illustrated in FIG. 3, a differential image is first acquired and then overlapped. However in the image acquiring method according to the present exemplary embodiment, overlapping is first performed and then a differential image is acquired. Such a difference will be described hereinafter.

Firstly, an image of a first region is acquired N times (herein, N is an integer of 2 or more) (S210). N frame images are consecutively acquired by the camera 111. In the present exemplary embodiment, the camera 111 has a frame rate of 15 fps. Therefore, it is possible to acquire 15 frames per second. That is, the present step is performed by acquiring images in the unit of frame for a predetermined period of time.

Then, the frame images acquired in the step S210 by an image process are summed in the unit of pixel, so that a first summed image is acquired (S220). This step may be performed by the control unit 150.

Then, the target 1 is moved to a second region different from the first region by the moving means 130 (S230). This step is the same as described above. Therefore, detailed explanation thereof will be omitted.

Then, an image of the second region is acquired M times (herein, M is an integer of 2 or more) (S240). The image acquiring method is the same as the step S210. Therefore, detailed explanation thereof will be omitted.

Then, frame images acquired in the step S240 by an image process are summed in the unit of pixel, so that a second summed image is acquired (S250). This step may be performed by the control unit 150.

Then, a differential image is acquired by subtracting, from either the first summed image or the second summed image, the other summed image (S260). A method for acquiring the differential image is the same as the step S130 illustrated in FIG. 3. Therefore, detailed explanation thereof will be omitted.

Accordingly, the same effect as illustrated in FIG. 3 can be expected, and the image as shown in FIG. 6b can be acquired.

Meanwhile, N and M do not need to be identical to each other, but in order to achieve an accurate reversal effect as illustrated in FIG. 7(b), preferably, N and M may be identical to each other.

Referring to FIG. 11(a), the exemplary embodiment of FIG. 10 can be performed by acquiring N frame images after positioning the first region in the west (i.e., on the left) and consecutively acquiring M frame images after positioning the second region in the east (i.e., on the right).

Otherwise, referring to FIG. 11(b), the exemplary embodiment of FIG. 10 can be performed by acquiring N frame images after positioning the first region in the west and consecutively acquiring M frame images after positioning the second region in the east, and then imaging the first region positioned in the west for a period of P frames and imaging the second region positioned in the east for a period of Q frames.

Alternatively, referring to FIG. 11(c), the exemplary embodiment of FIG. 10 can be performed by acquiring N frame images after positioning the first region in the west and consecutively acquiring M frame images after positioning the second region in the east, and then acquiring P frame images after positioning a third region in the north (i.e., on the upper side) and consecutively acquiring Q frame images after positioning a fourth region in the south (i.e., on the lower side). Herein, a differential image can be acquired by selecting two or more of a summed image of the first region, a summed image of the second region, a summed image of the third region, and a summed image of the fourth region.

The above-described M, N, P, and Q are integers of 2 or more. They do not need to be identical to one another, but in order to achieve the accurate reversal effect as illustrated in FIG. 7(b), preferably, M, N, P, and Q may be identical to one another.

Meanwhile, in the present exemplary embodiment, it has been described that the first region and the second region are separated from each other in a transverse direction and the third region and the fourth region are separated from each other in a vertical direction, but they are not limited thereto. The first region and the second region may be disposed in the vertical direction or may be separated from each other at a predetermined angle, and the third region and the fourth region may be disposed in the transverse direction or may be separated from each other at a predetermined angle. That is, positional relationships among the first region to the fourth region can be freely set.

The above-described image acquiring method and the image acquiring apparatus using the same can be used in an atomic force microscope. An atomic force microscope includes an optical vision system configured to optically observe a contact position of a cantilever on a surface of a target to be measured. The above-described image acquiring method can be applied to such an optical vision system.

Although the exemplary embodiments of the present invention have been described with reference to the accompanying drawings, it can be understood by a person having ordinary skill in the art that the present invention may be embodied in many different forms without departing from the technical concept or essential feature of the present invention. Therefore, it should be understood that the above-described exemplary embodiments are illustrative in all aspects and do not limit the present invention.

The invention claimed is:

1. An image acquiring method for acquiring an image using a measurement apparatus including an image acquiring means which acquires an image of a surface of a target to be measured in the unit of predetermined size pixels and a moving means capable of moving the target to be measured, the image acquiring method comprising:
    acquiring an image of a first region from the surface of the target to be measured through the image acquiring means;
    acquiring an image of a second region, which is different from the first region, by moving the target to be measured, through the moving means;
    acquiring a differential image by subtracting, from either the image of the first region or the image of the second region, the other image; and
    overlapping the differential image multiple times,
    wherein the image of the second region is acquired in a manner of overlapping a part of the image of second region with the image of the first region such that the overlapped part makes the differential image show inverted by change of a gradation value in the overlapped part, and
    a distance between the first region and the second region is smaller than a size of a target to be detected in order to form the overlapped part between the image of the first region and the image of the second region.

2. An image acquiring method for acquiring an image using a measurement apparatus including an image acquiring means which acquires an image of a surface of a target to be measured in the unit of predetermined size pixels and a moving means capable of moving the target to be measured, the image acquiring method comprising:
    acquiring an image of a first region from the surface of the target to be measured N times (herein, N is an integer of 2 or more) through the image acquiring means;
    acquiring a first summed image by summing N images of the first region;
    moving the target to be measured to a second region, which is different from the first region, through the moving means;
    acquiring an image of the second region from the surface of the target to be measured M times (herein, M is an integer of 2 or more) through the image acquiring means;
    acquiring a second summed image by summing M images of the second region; and
    acquiring a differential image by subtracting, from either the first summed image or the second summed image, the other summed image,
    wherein the image of the second region is acquired in a manner of overlapping a part of the image of second region with the image of the first region such that the overlapped part makes the differential image show inverted by change of a gradation value in the overlapped part, and
    a distance between the first region and the second region is smaller than a size of a target to be detected in order to form the overlapped part between the image of the first region and the image of the second region.

3. The image acquiring method of claim 1, wherein a distance between the first region and the second region is greater than a resolution of the image acquiring means.

4. The image acquiring method of claim 2, wherein the N is identical to the M.

5. An image acquiring apparatus comprising:
    an image acquiring means which acquires an image of a surface of a target to be measured in the unit of predetermined size pixels;
    a moving means capable of moving the target to be measured; and
    a control unit that receives the image from the image acquiring means and performs an image process, and controls an operation of the moving means,
    wherein the control unit processes the image of the surface of the target to be measured by acquiring an image of a first region from the surface of the target to be measured through the image acquiring means, acquiring an image of a second region, which is different from the first region, by moving the target to be measured, through the moving means, acquiring a differential image by subtracting, from either the image of the first region or the image of the second region, the other image, and overlapping the differential image multiple times,
    wherein the image of the second region is acquired in a manner of overlapping a part of the image of second region with the image of the first region such that the overlapped part makes the differential image show inverted by change of a gradation value in the overlapped part, and
    a distance between the first region and the second region is smaller than a size of a target to be detected in order to form the overlapped part between the image of the first region and the image of the second region.

6. An image acquiring apparatus comprising:
an image acquiring means which acquires an image of a surface of a target to be measured in the unit of predetermined size pixels;
a moving means capable of moving the target to be measured; and
a control unit that receives the image from the image acquiring means and performs an image process, and controls an operation of the moving means,
wherein the control unit processes the image of the surface of the target to be measured by acquiring an image of a first region from the surface of the target to be measured N times (herein, N is an integer of 2 or more) through the image acquiring means, calculating a first summed image by summing N images of the first region, moving the target to be measured to a second region, which is different from the first region, through the moving means, acquiring an image of the second region from the surface of the target to be measured M times (herein, M is an integer of 2 or more) through the image acquiring means, calculating a second summed image by summing M images of the second region, and calculating a differential image by subtracting, from either the first summed image or the second summed image, the other summed image,
wherein the image of the second region is acquired in a manner of overlapping a part of the image of second region with the image of the first region such that the overlapped part makes the differential image show inverted by change of a gradation value in the overlapped part, and
a distance between the first region and the second region is smaller than a size of a target to be detected in order to form the overlapped part between the image of the first region and the image of the second region.

7. The image acquiring apparatus of claim 5, wherein the image acquiring means is an imaging apparatus using a CCD or a CMOS.

8. The image acquiring method of claim 2, wherein a distance between the first region and the second region is greater than a resolution of the image acquiring means.

* * * * *